United States Patent [19]

Weidmann et al.

[11] Patent Number: 4,488,444
[45] Date of Patent: Dec. 18, 1984

[54] TESTING DEVICE FOR TENNIS RACQUETS

[76] Inventors: Ulrich Weidmann, Industriestrasse 13, CH-8152 Glattbrugg; Hans R. Weber, Althoossteig 11, CH-8046 Zurich, both of Switzerland

[21] Appl. No.: 449,010
[22] PCT Filed: Mar. 4, 1982
[86] PCT No.: PCT/CH82/00034
  § 371 Date: Nov. 22, 1982
  § 102(e) Date: Nov. 22, 1982
[87] PCT Pub. No.: WO82/03274
  PCT Pub. Date: Sep. 30, 1982

[30] Foreign Application Priority Data

Mar. 23, 1981 [CH] Switzerland ............... 1963/81

[51] Int. Cl.³ ............... G01L 5/06; G01N 3/20
[52] U.S. Cl. ............... 73/862.45; 73/65; 73/849

[58] Field of Search ............... 73/862.45, 862.47, 65, 73/849, 856

[56] References Cited

U.S. PATENT DOCUMENTS 2,299,722  10/1942  Burns et al. ............... 73/849 X

FOREIGN PATENT DOCUMENTS

| 2916735 | 11/1980 | Fed. Rep. of Germany ... 73/862.45 |
| 0567476 | 3/1924 | France ............... 73/862.45 |
| 0131380 | 2/1929 | Switzerland ............... 73/65 |
| 0381729 | 10/1932 | United Kingdom ............... 73/65 |

*Primary Examiner*—Charles A. Ruehl
*Attorney, Agent, or Firm*—Thomas W. Speckman

[57] ABSTRACT

Apparatus and process for separately measuring tension of strings, stiffness of frame in both strung and unstrung condition, and point of balance of a tennis racquet.

8 Claims, 5 Drawing Figures

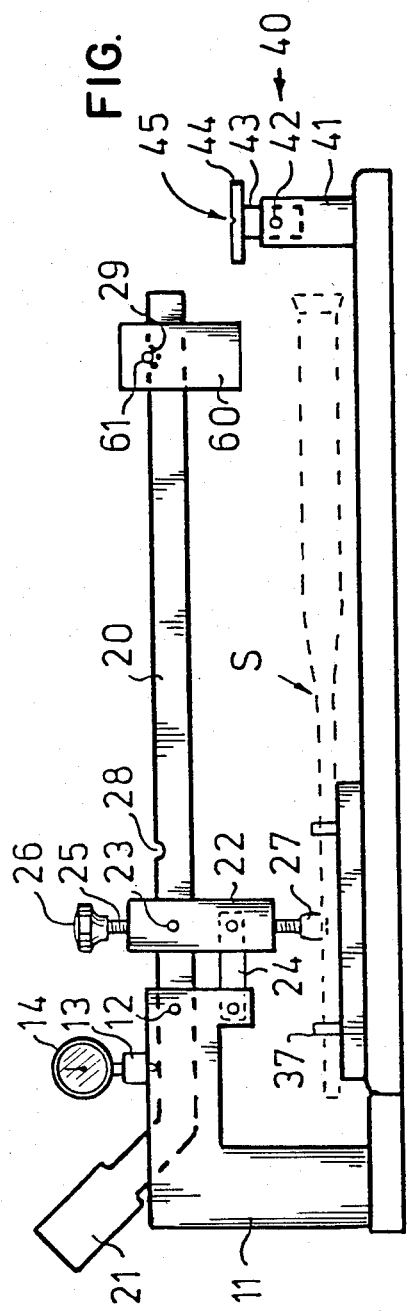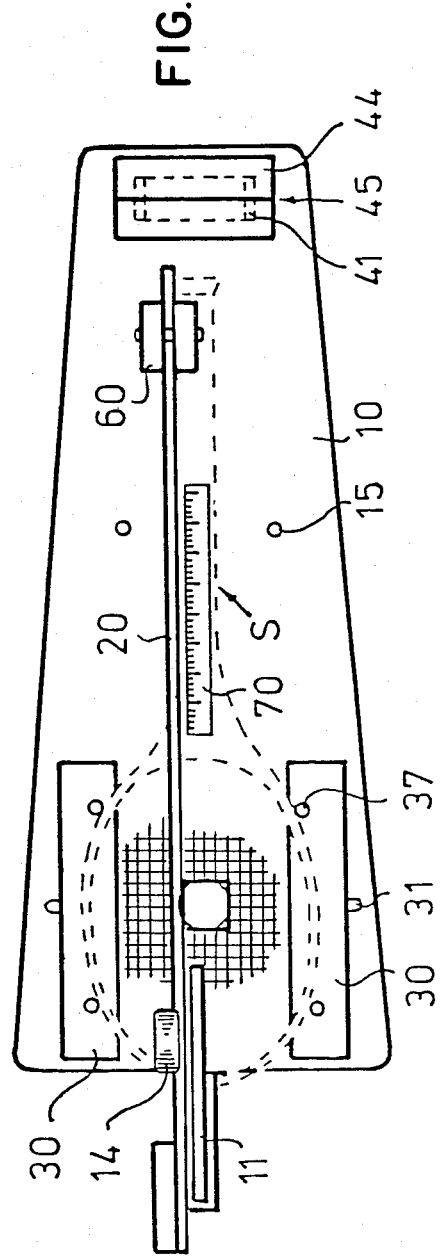

TESTING DEVICE FOR TENNIS RACQUETS

This invention relates to a testing device for tennis racquets to measure the tension of the stringing. The degree of tightness or stiffness of the strings of the hitting surface of a tennis racquet is subject to variation. The higher the tension or tightness of the strings, the stiffer the hitting surface. The stringing may be made from single stretched synthetic gut strings or from twisted multi-filament strings. Natural gut may be used instead of synthetic gut. Synthetic strings have a higher wear resistance. A stringing of synthetic gut reacts tight at hard strokes and soft at soft strokes.

The particular nature of the stringing is of critical importance. Depending on the player's handling of the racquet, the ball is bounced off the stringing and returned at varying speeds and spin. During this brief encounter lasting no longer than a few thousandths of a second, ball, stringing and racquet are temporarily deformed. Of the racquet, it is particularly the frame that is subjected to deformation. All these factors taken together, hardness of the ball, stiffness of the stringing, flexibility of the frame and handling of the racquet, determine the degree of ball control.

A tournament player usually possesses several racquets and uses his judgment as to which racquet is best suited for a match with a particullar opponent, the type of ball used and the condition of the court. Instead of estimating the tension of the stringing empirically, the advanced player will find it of advantage to be able to measure the tightness of the stringing accurately.

STATE OF THE ART

Several devices are known to measure the tension of racquet stringings. In one device, the stringmeter is attached to the frame itself and the tension of the stringing is measured by a weight loaded beam. This type of measurement has the disadvantage that the measuring result is not just a straight indication of the tension of the stringing, but it also includes the flexibility value of the frame.

OBJECT OF THE INVENTION

It is the object of the present invention to create a measuring device by which the prior disadvantage is overcome, so that the measuring result is a true indication of the tension of the strings, without also taking into account the stiffness of flexibility, resp. of the frame. Since the stiffness of the frame is of importance by itself, however, it is another object of the invention to measure the frame stiffness both in the strung and the unstrung condition of the racquet. Finally, a further object of the invention is to use the device for determining the balance point of the racquet.

THE INVENTION

The device according to the invention comprises a base plate with two detachable lateral supporting bars adjustable to accommodate and center the frame of a tennis racquet to be tested, a bracket block connected to the base plate and supporting a weight loaded beam pivotably mounted therein, the beam being provided with a plunger head directed onto the center of a strung frame to be tested, and a gauge attached to the bearing block with the plunger of the gauge resting on the beam.

For the purpose of measuring also the stiffness of the frame, be it strung or unstrung, it is of advantage that a supporting bar is detachably provided in the mid area of the base plate and transversely to its longitudinal direction, and that a counterbracket for the grip of a racquet to be tested is provided at the end of the base plate opposite the bracket block.

THE DRAWINGS

The drawings illustrate by way of example an embodiment of the device of the invention, which will be further described with reference to the drawings, in which:

FIG. 1 is a side view of the testing device of the invention during measurement of the tension of the stringing.

FIG. 2 is a top plan view of the device of FIG. 1.

Figure 3:
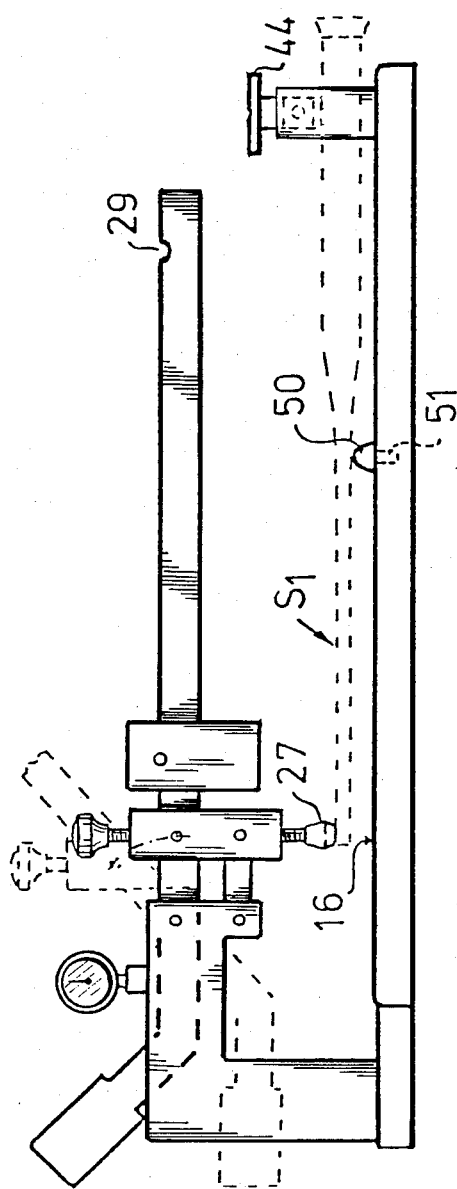
FIG. 3 shows the device of FIG. 1 in a modified condition for measuring the stiffness of the frame.

FIGS. 1 and 2 show the device in the condition for measuring the tension or tightness of the racquet stringing. The device comprises a base plate 10 in the shape of an elongate trapezoid. Mounted on the wide parallel side is a bracket block 11 to which a lever or beam 20 is pivotably secured at 12. Attached to the shorter arm of the lever is an equilibrium weight to offset in part the weight of the lever in its horizontal position. A block 22 is pivotably attached to the lever at 23. The lever or beam 20 is guided parallel to its vertical movements by means of a transverse member 24 pivotably connected to block 22 and bracket block 11. Extending through the block 22 is an adjusting threaded bolt 25 having a head 26 and at its bottom end a plunger 27. Secured to the bracket block 11 is a holding means for a gauge 14 whose measuring plunger is engaging the beam 20.

Figure 4:
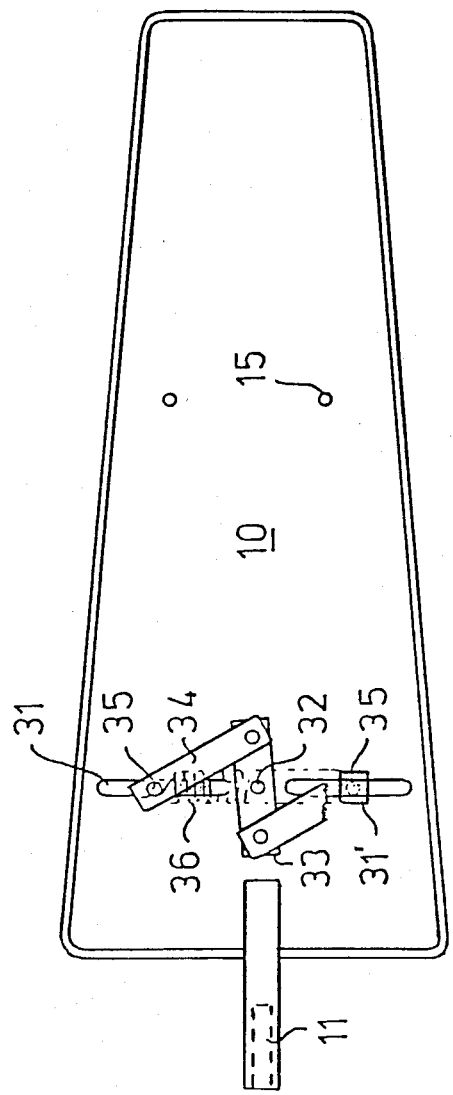
FIG. 4 shows the device of FIG. 1 in a view from below.

The distance between the pivot point 12 of the beam 20 and the pivot point 23 is equal to the distance between the pivot point 12 and the point of engagement of the beam 20 by the measuring plunger of the gauge 14 to enable the reading of the amount of descent of the plunger 27 on the gauge. The upper surface of the beam 20 is provided with two notches 28 and 29. Detachably mounted on the base plate 10 are two supporting bars 30. For the purpose of being removable, the bars 30 are provided with downwardly extending pegs, not illustrated, for engaging slides which are slidably guided in grooves 31 extending perpendicularly to the longitudinal axis of the base plate. To ensure that the bars 30 are always equally spaced from the center line of the base plate, as they are being adjustably displaced, the slides 31' are provided with a guide linkage located under the base plate, as it is shown in FIG. 4. The pivot point 32 is fixedly connected to the base plate 10 and supports a lever 33 having two arms of equal length. Pivotably jointed to the lever 33 are two latches 34 which are linked by pins 35 to the slides 31' guided in the grooves 31. The lower ends of the pins 35 are connected by a torsion spring.

On their upper surfaces, each of the supporting bars is provided with two upwardly extending pegs 37 for centering the frame of a tennis racquet positioned upon the supporting bars.

In the area of its narrow parallel side, the base plate 10 has attached thereto a counterbracket or abutment 40 comprising bearings 41 and a bridge 43 pivotable about a horizontal axis 42. The upper end of the bridge 43 carries a support surface 44 which is provided with line markings 45 extending parallel to the pivot axis 42.

The base plate 10 has bores 15 in the area between the bracket block 11 and the counterbracket 40 for receiving pegs 51 of a bracing bar 50 extending across the longitudinal expanse of the base plate.

Finally, 60 designates a weight having a deep groove and a pin 61 extending transversely thereto, and 70 represents a scale applied to the base plate 10.

Figure 5:
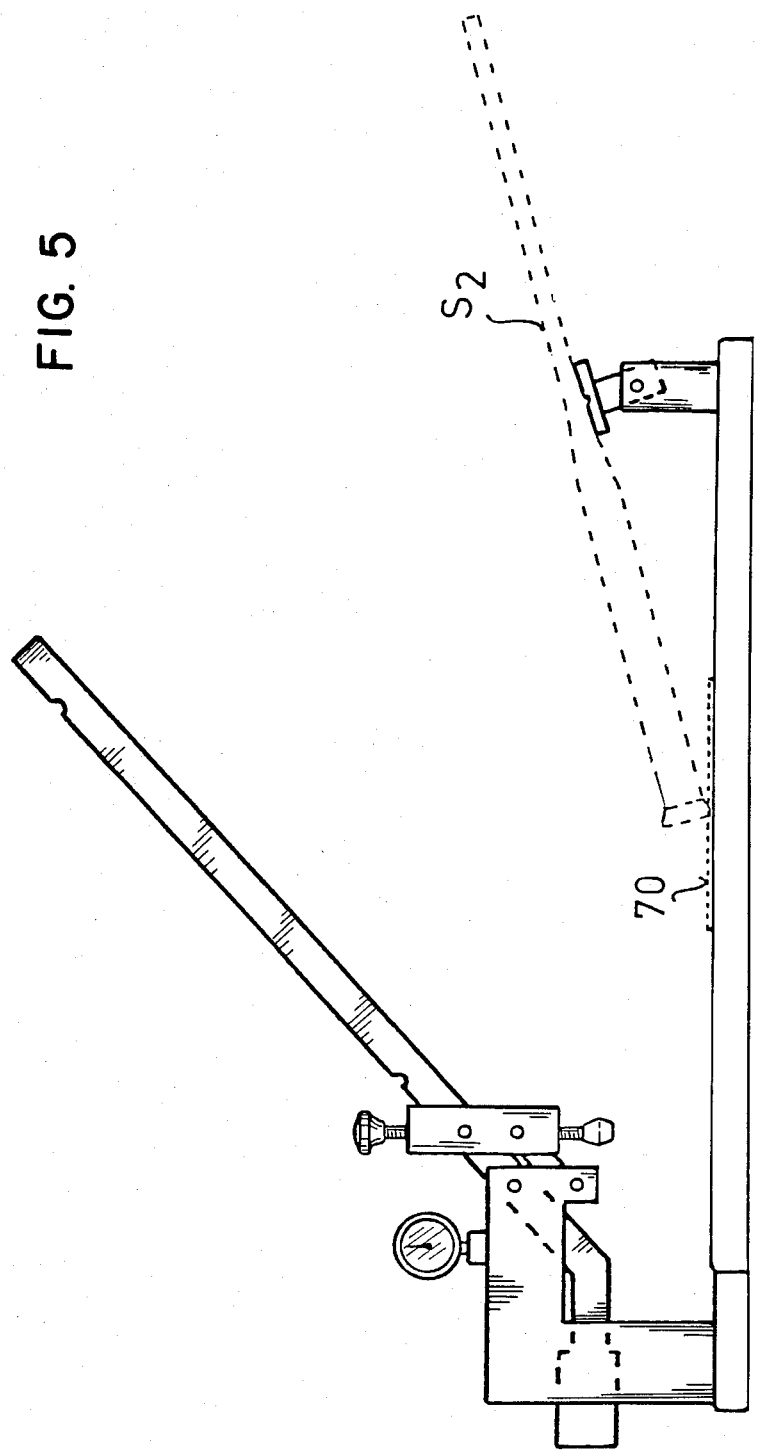
FIG. 5 shows the device of FIG. 1 as used for locating the balance point of a tennis racquet.

When not in use, i.e. in the inoperative position, the beam is raised up at an angle of about 45°, as it is shown in FIG. 5. It is retained in this position by a latch or a magnet.

Application of the device for measuring the tension of the stringing (FIGS. 1 and 2)

A tennis racquet S is placed upon the two spaced supporting bars 30, with the pegs 37 serving to center the frame so that the middle of the frame is positioned under the plunger 27. Thereupon, the lever 20 is carefully moved downward until the plunger 27 touches the stringing. The weight of the lever 20, being partly compensated for by the counterweight 21, produces a pretension of approximately 2 kilograms. This pretension has the effect that the frame is snugly held against the supporting bars 30 to obtain accurately reproducible and reliable measuring results. Turning the set screw 25 by means of the head 26 will set the gauge to zero. Now the weight 60 is slidably attached to the beam 20 until the pin 61 engages the notch 29. In this position, the stringing is under full load and the lowering depth of the sliding head or plunger is readable on the gauge 14. The stiffer the stringing is, the shorter is the descent of the plunger 27. In this manner, the measurement of the tension of the stringing is accurately reproducible and recordable.

Application of the device for measuring the stiffness of the frame (FIG. 3)

To measure the stiffness of the frame, the device needs to be readjusted to some extent. First, the two supporting bars 30 must be removed. Then, depending on the size of the frame, the bracing bar 50 is installed, with its centering pegs 51 being inserted into the holes 15 either in front or in back. The grip of the racquet S 1 is moved underneath the bridge 43 of the counterbracket 40 a distance up to a line marking 16 on the base plate. In this manner, the head portion of the frame comes to lie under the plunger 27. The bracing bar 50 is located in the area between the frame head and the grip. Now the plunger is lowered until it is caused by the weight of the beam 20 to come to rest upon the frame edge at approximately 2 kilogram pretension. Again, the plunger 27 is adjusted until the gauge, at this pretension, reaches the zero position. Since the lever arm with the attached load is much longer in this instance, the load exerted by the weight 60 must not be too great. Therefore, the weight 60 is moved up to the notch 28, and the lowering distance of the plunger 27 may be read on the gauge. The stiffer the frame, the smaller the lowering of the plunger.

Application of the device for locating the balance point of a Racquet FIG. 5)

For locating the balance point of a racquet S 2, the racquet is placed upon the support surface 44, with the grip pointing toward the base plate. Then the tennis racquet is slidably displaced until it is just about in the tipped position and the grip is able to lower itself slowly onto the base plate, so that the grip end comes to rest almost without pressure on the scale applied to the base plate 10 (see FIGS. 1 and 5). This scale indicates directly the location of the balance point, that is, its distance from the grip end.

We claim:

1. A testing device for tennis racquets to measure the tension of the stringing, comprising a base plate (10) with two detachable lateral supporting bars (30) adjustable to accommodate and center the frame of a tennis racquet to be tested, a bracket block (11) connected to the base plate and supporting a weight loaded beam (20) pivotably mounted therein, said beam being provided with a plunger (27) directed onto the center of a strung frame to be tested, and a gauge (14) attached to said bracket block with the plunger of said gauge resting on said beam (20).

2. Testing device according to claim 1, characterized in that an adjustable bracing bar is detachably provided in the mid area of said base plate (10) and transversely to its longitudinal axis, and that a counterbracket (40) for the grip of said racquet to be tested is provided at the end of said base plate opposite said bracket block.

3. Testing device according to claim 2, characterized in that said counterbracket (40) comprises a bridge (43) between two bearings (41) secured to said base plate in a manner as to be pivotable about a horizontal axis (42), said bridge carrying on top a support surface (44) having a line marking (45) thereon which extends parallel to the pivot axis, and said base plate is provided with a scale (70) in its central portion along its long axis.

4. Testing device according to claim 1, characterized in that said plunger (27) is connected to said bracket block (11) by parallel guide means (24).

5. Testing device according to claim 1, characterized in that a pivot point (23) of said plunger (27) is spaced in front of a pivot bearing (12) of said beam (20) a distance which is equal to the distance of the point of contact of said plunger of said gauge (14) with said beam (20) in rear of said pivot bearing.

6. Testing device according to claim 1, characterized in that said supporting bars (30) are moved vertically to their longitudinal direction in slots (31) provided in said base plate (10), and that a guide mechanism (32-36) is provided under said base plate which guide mechanism is adapted to control the contrary motion of said bars by means of pins (35) extending through said slots (31) and engaging said bars (30).

7. Process for measuring the tension of the stringing of a tennis racquet using an apparatus comprising a base plate (10) with two detachable lateral supporting bars (30) adjustable to accommodate and center the frame of a tennis racquet to be tested, a bracket block (11) connected to the base plate and supporting a weight loaded beam (20) pivotably mounted therein, said beam being provided with a plunger (27) directed onto the center of a strung frame to be tested, and a gauge (14) attached to said bracket block with the plunger of the gauge resting on said beam (20), said process comprising the following steps:

(a) Placing a strung racquet frame upon, and centering it by said supporting bars (30);

(b) Lowering said beam (20) until said plunger (27) rests on said stringing, whereby the weight of said beam produces a pretension;

(c) Setting said gauge (14) to zero;
(d) Suspending a weight (60) from said beam (20) on the side of plunger (27) away from said pivotal mounting;
(e) Recording the lowering distance of said plunger (27) on said gauge.

8. Process for measuring the stiffness of a strung or unstrung tennis racquet frame using an apparatus comprising a base plate (10), a bracket block (11) connected to said base plate and supporting a weight loaded beam (20) pivotably mounted therein, said beam being provided with a plunger (27) directed onto the frame to be tested, and a gauge (14) attached to said bracket block with the plunger of the gauge resting on said beam (20), a bracing bar (50) is detachably provided in the mid area of said base plate (10) and transversely to its longitudinal axis, and a counterbracket (40) for the grip of said racquet to be tested provided at the end of said base plate opposite said bracket block, said process comprising the following steps:

(a) Placing the grip of said racquet to be tested underneath said counterbracket (40) up to a line marking (16) so that the top edge of said frame is positioned under said plunger (27);
(b) Lowering said beam (20) until said plunger (27) engages said top edge of said frame, whereby the weight of said beam produces a pretension;
(c) Setting said gauge (14) to zero;
(d) Suspending a weight (60) from said beam (20);
(e) Recording the lowering distance of said plunger (27) on said gauges.

* * * * *